(12) United States Patent
Andersson et al.

(10) Patent No.: US 6,835,379 B2
(45) Date of Patent: Dec. 28, 2004

(54) METHOD OF PRODUCING IGG

(75) Inventors: Inger Andersson, Storvreta (SE); Lars-Olof Lindquist, Uppsala (SE)

(73) Assignee: Amersham Biosciences AB, Uppsala (SE)

( * ) Notice: Subject to any disclaimer, the term of this patent is extended or adjusted under 35 U.S.C. 154(b) by 212 days.

(21) Appl. No.: 10/220,929

(22) PCT Filed: Mar. 29, 2001

(86) PCT No.: PCT/EP01/03624

§ 371 (c)(1), (2), (4) Date: Dec. 9, 2002

(87) PCT Pub. No.: WO01/72844

PCT Pub. Date: Oct. 4, 2001

(65) Prior Publication Data

US 2003/0143222 A1 Jul. 31, 2003

(30) Foreign Application Priority Data

Mar. 30, 2000 (SE) .............................................. 0001128

(51) Int. Cl.[7] ..................... A61K 39/395; C07K 16/00; C07K 1/18
(52) U.S. Cl. ................................. 424/130.1; 435/176.1
(58) Field of Search ........................... 424/130.1, 176.1; 530/387.1

(56) References Cited

U.S. PATENT DOCUMENTS

| | | | |
|---|---|---|---|
| 5,164,487 A | 11/1992 | Piechaczek et al. | 530/389.1 |
| 5,410,025 A | 4/1995 | Piechaczek et al. | 530/390.5 |
| 5,429,746 A * | 7/1995 | Shadle et al. | 210/635 |
| 5,593,675 A | 1/1997 | Hodler et al. | 424/130.1 |
| 6,281,336 B1 * | 8/2001 | Laursen et al. | 530/390.1 |
| 6,307,028 B1 * | 10/2001 | Lebing et al. | 530/390.1 |

FOREIGN PATENT DOCUMENTS

| | | |
|---|---|---|
| DE | 41 18 912 | 7/1992 |
| WO | WO 99/18130 | 4/1999 |
| WO | WO 99/64462 | 12/1999 |

OTHER PUBLICATIONS

C. Ostund "Large–scale purification of monoclonal antibodies" TIBTECH, Nov. 1986 pp. 288–293.

* cited by examiner

Primary Examiner—Herbert J. Lilling
(74) Attorney, Agent, or Firm—Royal N. Ronning, Jr.; Stephen G. Ryan; Yonggang Ji

(57) ABSTRACT

A method for producing IgG from plasma for medical applications, comprising at least: (i') removal of albumin resulting in an IgG fraction, (ii') purifying IgG from an IgG fraction, which is derived from the IgG fraction obtained in step (i'), by adsorbing IgG to a cation exchanger and collecting the adsorbed IgG fraction, and (iii') virus inactivation in an IgG fraction derived from the IgG fraction collected in step (ii'). The method is characterized in; (I) concentrating the IgG fraction obtained in step (i'), (II) adjusting pH to 4±0.1 in the IgG fraction released from the cation exchanger in step (ii'), and preferably maintaining the pH below 6.0 during the remaining steps of the method; and (III) carrying out the virus inactivation (step iii') by using chemicals at a temperature of 30° C.±2° C. for at least 4 hours. Anticomplementary activity is typically below 1 $CH_{50}$/mg immunoglobulin.

7 Claims, 1 Drawing Sheet

Figure 1.

Fresh frozen plasma without coagulation factors

Sephadex G25

Euglobulin precipitation

DEAE Sepharose FF

Ultrafiltration

Q Sepharose FF

CM Sepharose FF pH adjustment to pH 4 ± 0.1

Ultrafiltration

Virusinactivation at 30 °C for 4-16 h

CM Sepharose FF

Ultrafiltration

Diafiltration to 0.5 ± 0.1 mS

Formulation

Sterile filtration

METHOD OF PRODUCING IGG

FIELD OF THE INVENTION

The present invention relates to a method of producing IgG for medical applications. The method of the invention provides an IgG product having low anticomplementary activity (ACA).

BACKGROUND OF THE INVENTION

IgG prepared from human plasma is widely used in the treatment of agammaglobulinaemia, idiopathic thrombocytopenic purpura and in the prophylaxis of certain diseases. IgG preparations are administered intramuscularly as well as intravenously.

Within the field of the art it is well known that isolated IgG preparations have marked anticomplementary activities (ACA). It has been shown that the components responsible for these activities are aggregates of IgG that form either spontaneously or as a result of the isolation procedure. These anticomplementary aggregates have been shown to be harmful in several clinical applications of the IgG products. For example, intravenous administration of IgG preparations can give rise to adverse side reactions, including anaphylactic shock.

Several solutions have been proposed to overcome the problem with ACA in IgG preparations. For example, in U.S. Pat. No. 3,966,906 a process is described for treating a crude gamma globulin fraction of serum with pepsin to disaggregate IgG and reduce anticomplement activity. However, the therapeutic effect provided by such a preparation is unacceptably short since it is rapidly excreted. Another drawback with the pepsin treated immunoglobulins is that their Fc binding capacity is lower than for native immunoglobulins.

Attempts have been made to stabilise pepsin treated IgG preparations, such as by polyethylene glycol (PEG) see for example WO 86/06993.

To solve the problem with high ACA activity it has been proposed to chemically modify the IgG preparations. For example, in U.S. Pat. No. 3,902,262 a portion of the disulphide linkages of the IgG molecule is reduced to —SH groups and then the —SH groups are alkylated.

For obvious reasons, it would be desirable to have an IgG product which is free from enzymatic and other chemical modification and to be as close to native as possible. A method fulfilling these criteria has been described in "An improved chromatographic method for production of IgG from human plasma" by I. Andersson, L-O Lindquist, J. Berglöf, presented at the "XXIII Congress of the ISBT", Amsterdam, The Netherlands, Jul. 2–8, 1994). However, this procedure also shows unsatisfactory high ACA-levels and does not fulfil the FDA and EU requirements for intravenous drugs.

Known methods for the manufacture of IgG compositions typically comprise several steps selected amongst:

a) buffering plasma, for instance either by subjecting the plasma to an appropriate gel filtration chromatography or by diafiltration;
b) removing euglobulins, such as by precipitation;
c) removing the albumin fraction (albumin), for instance by binding albumin and the like to an anion exchanger leaving the IgG in the unbound fraction (IgG fraction);
d) purifying, after removal of euglobulins and albumin, the IgG fraction obtained in step (c) on an anion exchanger and collecting the unbound fraction;
e) purifying the plasma fraction obtained in step (d) on a cation exchanger and collecting the bound fraction (adsorption and release of IgG);
f) concentrating the IgG enriched plasma fraction obtained in step (e) (IgG released from the cation exchanger), preferably by ultrafiltration;
g) inactivating viruses by adding virus inactivation chemicals, preferably a solvent/detergent (S/D) solution, to an IgG enriched plasma fraction, for instance the fraction obtained in step (f);
h) removing the virus antiviral chemicals added in step (g), preferably by adsorbing IgG to a cation exchanger and releasing and collecting the bound fraction;
i) concentrating the bound fraction collected in step (h), for instance by ultrafiltration;
j) formulating of the fraction concentrated in step (i);
k) sterile filtration of the formulated IgG obtained in step (k).

SUMMARY OF THE INVENTION

The present invention provides a solution for producing IgG products having reduced ACA, by modifying earlier known methods.

Thus in a first aspect the invention relates to a method of producing IgG from plasma for medical applications, comprising at least: (i') removal of albumin resulting in an IgG fraction, (ii') purifying IgG from an IgG fraction, which is derived from the IgG fraction obtained in step (i'), by adsorbing IgG to a cation exchanger and collecting the adsorbed IgG fraction, and (iii') virus inactivation in an IgG fraction derived from the IgG fraction collected in step (ii'). The method is characterized in (I) concentrating the IgG fraction obtained in step (i'),
(II) adjusting pH to 4±0.1 of the IgG fraction released from the cation exchanger used in step (ii'), and preferably maintaining the pH below 6.0 during the remaining steps of the method; and
(III) carrying out the virus inactivation (step iii') by using virus inactivation chemicals, preferably a solvent/detergent (S/D) solution, at a temperature of 30° C.±2° C. for at least 4 hours.

Adjustment of pH to around 4 in (II) permits virus inactivation to be carried out at around 30° C. In the corresponding earlier process, in which pH was 5,5, the level of the proteolytic activity at 30° C. was unacceptable.

A preferred variant of the process according to the invention comprises steps (a)–(k) above in which the albumin removal step (c) corresponds to (i'), the cation exchange step (e) corresponds to (ii'), and the virus inactivation (g) corresponds to (iii').

The purification and/or removal steps above are preferably run as chromatography. Appropriate separation media used in these steps are hydrophilic in the sense that they are able to expose surfaces carrying hydrophilic groups, such as hydroxy, amido etc., to the liquid sample containing IgG. Appropriate separation media may be found amongst those that are based on synthetic polymers and/or biopolymers (for instance polysaccharides) carrying hydrophilic groups, as referred to above. Depending on where in the process the media is to be applied they may be uncharged, or may carry positively charged (e.g. ammonium groups) and/or negatively charged groups (e.g. carboxy groups and sulphonic acid groups). The following chromatographic media are preferred:

step a): Sephadex G25;
step c): DEAE Sepharose FF;

step d): Q Sepharose FF;

step e): CM Sepharose FF;

step h): CM Sepharose FF.

Sephadex and Sepharose (Amersham Pharmacia Biotech AB, Uppsala, Sweden) are based on cross-linked dextrand and agarose, respectively. DEAE means that the base matrix (cross-linked dextran is substituted with diethylaminoethyl groups. Analogously Q stands for quaternary ammonium groups, and CM for carboxy methyl groups.

The concentrating according to (I) is preferably performed immediately after albumin removal (for instance after step c as defined above) by ultrafiltration, to less than or equal to the volume of the starting plasma.

To be able to use an acetate buffer in the step for removal of virus inactivation chemicals (step h), the ionic strength is adjusted to about 1.40 mS before this step.

In a preferred embodiment, the method also comprises, in step (i) lowering of ionic strength to 0.5 mS±0.1, preferably by diafiltration against distilled water.

DETAILED DESCRIPTION OF THE INVENTION

Below the invention will be described in more detail in association with the accompanying drawing, FIG. 1, which schematically shows a preferred embodiment of the method according to the invention, wherein the characterising features of the method as defined in the claims are in bold letters.

Starting Material

Both Recovered Plasma, Fresh Frozen Plasma and Source plasma can be used as starting material.

The following subclasses of plasma can be identified and used as starting material.

1. Cryosupernatant plasma that has passed a chromatographic step for adsorption of vitamin K dependent factors (FIX, prothrombin, FVII, FX).
2. Cryosupernatant plasma from which the prothrombin complex has not been removed.
3. Plasma that has passed a gel filtration medium (preferably having exclusion limits in the same range as Sepharose 4FF (Amersham Pharmacia Biotech AB, Uppsala, Sweden) for removal of FVIII and that has passed a chromatographic step for adsorption of vitamin K dependent factors (FIX, prothrombin, FVII, FX).
4. Plasma that has passed a gel filtration medium for removal of FVIII and from which the prothrombin complex has not been removed.

The gel filtration medium preferably exclusion limits in the same range as Sepharose FF (Amersham Pharmacia Biotech AB).

In addition the starting material could also be free from ATIII and/or Fibrinogen.

Below two non-limiting Examples of methods according to the invention to purify IgG are described. The methods are performed at room temperature, if nothing else is stated.

Anticomplementary activity (ACA) refers to measurements in the final product, is measured according to Eur. Pharmacopoeia Monograph (1997) page 963 (2.6.17) and should not be higher than 1 $CH_{50}$/mg immunoglobulin.

EXAMPLE 1

625 L of thawed plasma is buffer exchanged into a 0.005 M NaAc (sodium acetate) pH 7 on a column of diameter Di=800 mm and bed height of H=600 mm, packed with Sephadex G-25 C. The flow is more than 100 cm/h, preferably 300 cm/h corresponding to a flow rate of 1500 L/h.

The eluted plasma is collected in a tank and 1 M acetic acid is added during stirring until the pH 5.2 is reached. The plasma is left standing without stirring for 4–12 hours at a temperature of 4–10° C. After standing the formed euglobulin precipitation is removed by centrifugation.

The plasma is adjusted with 1M NaAc, pH 5.2 to a final ionic strength of I=1.4 mS (Range I=1.30–1.50). The pH shall be between 5.15–5.25.

The plasma is applied in 6 cycles, 25–30 g of albumin per liter gel, on a column of Di=1000 mm and H=150 mm, packed with DEAE Sepharose FF and equilibrated with 0.020 M NaAc, pH 5.2. The linear flow rate is more than 60 cm/h, preferably 120 cm/h corresponding to a flow rate of 942 L/h. In the equilibration buffer the IgG will pass the column whilst the albumin is adsorbed. After 3 cycles the column is washed with 1.7 Vc (Vc=bed volume) of 0.15 M NaAc pH 4.0+0.5 M NaCl, 0.5 Vc of 0.5 M NaOH and 1.7 Vc of 0.15 M NaAc pH 4.0.

The IgG fraction of about 2350 L is concentrated by ultrafiltration to a final volume less or equal to 625 L, preferably 400–500 L. The procedure shall be started at the latest, when the whole fraction is collected from the DEAE Sepharose column.

The IgG solution is pH adjusted to pH 6.5 (6.45–6.55) with 1M NaOH and the ionic strength is adjusted to 1.40 mS (1.30–1.50 mS) by adding of WFI water (WFI=water for injection).

The IgG solution is applied in 6 cycles on a column of Di=1000 mm and H=150 mm, packed with Q Sepharose FF and equilibrated with 0.020 M NaAc, pH 6.5. Linear flow rate is more than 30 cm/h preferably 100 cm/h corresponding to 785 L/h. After 3 cycles the column is washed with 0.5 Vc of 0.5 M NaOH and 1.7 Vc of 0.15 M NaAc pH 4.0 The break through fraction containing IgG is directly adsorbed on the next column of Di=800 mm and H=80 mm and packed with CM Sepharose FF. When the IgG fraction from all 6 cycles has been pumped through, the column is washed with 10 Vc of 0.01 M Glycine buffer, pH 7.0. The IgG is then eluted with 7 Vc of 0.1 M Glycine+0.15 M NaCl pH 9.0.

The pH of the solution is adjusted to 4.0±0.1 with 1M HAc (Acetic acid) and concentrated by ultrafiltration to about 5% IgG.

Virus inactivation chemicals, Triton X-100 and TNBP, are added to the IgG solution during stirring. This mixture is transferred to the incubation tank for heat treatment at 30° C.±2° C. for 4–16 hours. The ionic strength of the solution is adjusted to 1.40 mS by dilution with WFI and applied in 1 cycle on another column of Di=800 mm and H=80 mm, packed with CM Sepharose FF and equilibrated with 0.020 M NaAc buffer pH 4.0. The linear flow rate is more than 40 cm/h, preferably 80 cm/h, corresponding to 400 L/h. After application the column is washed with 10 Vc of 0.01 M Glycine buffer pH 7.0 in order to remove the inactivation chemicals. The IgG is eluted with 7 Vc of 0.1 M Glycine+ 0.15 M NaCl pH 9.0 at the same flow rate and adjusted to pH 4.0 with 1M HCl. The solution is then concentrated by ultrafiltration to 5% to 7% IgG and the ionic strength is adjusted by diafiltration to 0.5 mS±0.2 mS. Finally the solution is adjusted to 5.0%.

The solution is formulated to the following composition:

Sucrose 1 g/g IgG

IgG 5% pH 4.0.

ionic strength 0.5 mS±0.2 mS

After sterile filtration, filling and capping the solution is ready for delivery or storage.

ACA for different batches measured as defined above was found to be 0.5–0.7 $CH_{50}$/mg immunoglobulin.

EXAMPLE 2

625 L of thawed plasma is buffer exchanged into a 0.005 M NaAc (sodium acetate) pH 7 on a column of diameter Di=800 mm and bed height of H=600 mm, packed with Sephadex G-25 C. The flow is more than 100 cm/h, preferably 300 cm/h corresponding to a flow rate of 1500 L/h.

The eluted plasma is collected in a tank and 1M acetic acid is added during stirring until the pH 5.2 is reached. The plasma is left standing without stirring for 4–12 hours at a temperature of 4–10° C. After standing the formed euglobulin precipitation is removed by centrifugation.

The plasma is adjusted with 1M NaAc, pH 5.2 to a final ionic strength of I=1.4 mS (Range I=1.30–1.50). The pH shall be between 5.15–5.25.

The plasma is applied in 6 cycles, 25–30 g of albumin per liter gel, on a column of Di=1000 mm and H=150 mm, packed with DEAE Sepharose FF and equilibrated with 0.020 M NaAc, pH 5.2. The linear flow rate is more than 60 cm/h, preferably 120 cm/h corresponding to a flow rate of 942 L/h. In the equilibration buffer the IgG will pass the column whilst the albumin is adsorbed. After 3 cycles the column is washed with 1.7 Vc (Vc=bed volume) of 0.15 M NaAc pH 4.0+0.5 M NaCl, 0.5 Vc of 0.5 M NaOH and 1.7 Vc of 0.15 M NaAc pH 4.0.

The IgG fraction of about 2350 L is concentrated by ultrafiltration to a final volume less than or equal to 625 L, preferably 400ñ500 L. The procedure shall be started at the latest, when the whole fraction is collected from the DEAE Sepharose column.

The IgG solution is pH adjusted to pH 6.5 (6.45–6.55) with 1M NaOH and the ionic strength is adjusted to 1.40 mS (1.30–1.50 mS) by adding of WFI water (WFI=water for injection).

The IgG solution is applied in 4 cycles on column of Di=1000 mm and H=150 mm, packed with a mixed bed of DEAE Sepharose FF and Arginine Sepharose FF in a proportion 60%/40% and equilibrated with 0.020 M NaAc, pH 6.5. Linear flow rate is more than 30 cm/h, preferably 100 cm/h corresponding to 785 L/h. After 2 cycles the column is washed with 0.5 Vc of 0.5 M NaOH and 1.7 Vc of 0.15 M NaAc pH 4.0. The break through fraction containing IgG is directly adsorbed on the next column of Di=800 mm and H=80 mm, packed with CM Sepharose FF. When the IgG fraction from all 6 cycles has been pumped through, the column is washed with 10 Vc of 0.01 M Glycine buffer, pH 7.0. The IgG is then eluted with 7 Vc of 0.1 M Glycine+0.15 M NaCl pH 9.0.

The pH of the solution is adjusted to 4.0±0.1 with 1M HAc (Acetic acid) and concentrated by ultrafiltration to about 5% IgG.

Virus inactivation chemicals, Triton X-100 and TNBP, are added to the IgG solution during stirring. This mixture is transferred to the incubation tank for heat treatment at 30° C.±2° C. for 4–16 hours. The ionic strength of the solution is adjusted to 1.40 mS by dilution with WFI and applied in 1 cycle on another column of Di=800 mm and H=80 mm, packed with CM Sepharose FF and equilibrated with 0.020 M NaAc buffer pH 4.0. The linear flow rate is more than 40 cm/h, preferably 80 cm/h corresponding to 400 L/h. After application the column is washed with 10 Vc of 0.01 M Glycine buffer pH 7.0 in order to remove the inactivation chemicals. The IgG is eluted with 7 Vc of 0.1 M Glycine+ 0.15 M NaCl pH 9.0 at the same flow rate and adjusted to pH 4.0 with 1M HCl. The solution is then concentrated by ultrafiltration to 5% to 7% IgG and the ionic strength is adjusted by diafiltration to 0.5 mS±0.2 mS. Finally the solution is adjusted to 5.0%.

The solution is formulated as in Example 1. After sterile filtration, filling and capping, the solution is ready for delivery or storage. ACA for different batches measured as defined above was found to be 0.5–0.7 $CH_{50}$/mg immunoglobulin.

What is claimed is:

1. In a method for producing IgG from plasma for medical applications, comprising: (i') removing any albumin, resulting in an IgG fraction, (ii') purifying IgG from said IgG fraction, by adsorbing IgG to a cation exchanger and collecting the adsorbed IgG fraction, and (iii') inactivating any virus in said purified IgG wherein the improvement comprises (I) concentrating the IgG fraction obtained in step (i'), (II) adjusting pH to 4±0.1 in the IgG released from the cation exchanger in step (ii'), and maintaining the pH below 6.0 during the remaining steps of the method; and (III) carrying out the virus inactivation (step iii') by using chemicals at a temperature of 30° C.±2° C. for at least 4 hours.

2. The method of claim 1 further comprising the steps:

a) buffering of fresh plasma;

b) removing any euglobulins;

c) purifying of plasma fraction obtained after removal of euglobulins and albumin on an anion exchanger and collecting the unbound plasma fraction (IgG fraction);

d) purifying of the IgG fraction obtained in step (c) on a cation exchanger and collecting the bound lgG plasma fraction including adjusting pH as in claim 1;

e) concentrating the IgG plasma fraction collected in step (d);

f) inactivating any virus as defined in (III) of claim 1 in the IgG plasma fraction collected in step (e);

g) removing any virus inactivation chemicals added in step (f) by adsorbing IgG to a cation exchanger and releasing and collecting the bound lgG plasma fraction;

h) concentrating of the IgG plasma fraction collected in step (g);

i) formulating of the IgG plasma fraction concentrated in step (h); and j) sterile filtering of the formulated IgG plasma fraction obtained in step (i).

3. The method of claim 1, wherein the concentration is performed by ultrafiltration to less than the volume of the starting plasma.

4. The method of claim 2, further comprising an adjustment of ionic strength to about 1.40 mS before step g).

5. The method of claim 2, wherein an acetate buffer is used in step g).

6. The method of claim 1, further comprising lowering after step iii' ionic strength to 0.5 mS±0.1.

7. The method of claim 6, wherein the lowering of the ionic strength is by diafiltration against distilled water.

* * * * *